(12) United States Patent
Terada et al.

(10) Patent No.: US 8,158,086 B2
(45) Date of Patent: Apr. 17, 2012

(54) POLYISOCYANATE PRODUCTION SYSTEM AND GAS TREATMENT APPARATUS

(75) Inventors: Kouichirou Terada, Omuta (JP);
Takashi Yamaguchi, Omuta (JP);
Takuya Saeki, Omuta (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 12/539,655

(22) Filed: Aug. 12, 2009

(65) Prior Publication Data

US 2009/0293732 A1    Dec. 3, 2009

Related U.S. Application Data

(62) Division of application No. 11/597,756, filed as application No. PCT/JP2006/305344 on Mar. 17, 2006, now Pat. No. 7,718,145.

(30) Foreign Application Priority Data

Apr. 5, 2005 (JP) .................................. 2005-108592
Apr. 5, 2005 (JP) .................................. 2005-108593

(51) Int. Cl.
*B01J 8/00* (2006.01)
*B01J 10/00* (2006.01)
*B01J 19/00* (2006.01)
*B01J 19/18* (2006.01)

(52) U.S. Cl. ........ 422/600; 422/129; 422/132; 422/134; 422/187; 422/608; 422/609; 422/611

(58) Field of Classification Search ................ 422/105, 422/132, 134, 168–170, 187, 189, 600, 608, 422/609, 611, 129; 96/256, 262; 568/306; 523/142

See application file for complete search history.

(56) References Cited

U.S. PATENT DOCUMENTS

| 2,418,931 | A |   | 4/1947  | Gurin |
| 4,557,877 | A | * | 12/1985 | Hofstetter ...................... 261/97 |
| 4,565,216 | A |   | 1/1986  | Meier |
| 4,774,070 | A |   | 9/1988  | Itoh et al. |
| 4,980,144 | A | * | 12/1990 | Koto et al. .................... 423/406 |
| 5,074,331 | A | * | 12/1991 | Kassarjian ................ 137/561 A |
| 5,715,173 | A |   | 2/1998  | Nakajima et al. |

(Continued)

FOREIGN PATENT DOCUMENTS

JP    55-047117 A    4/1980

(Continued)

OTHER PUBLICATIONS

Machine translation of JP 09075916 A, which was published on Mar. 25, 1997.*

(Continued)

*Primary Examiner* — Walter D Griffin
*Assistant Examiner* — Natasha Young
(74) *Attorney, Agent, or Firm* — Buchanan Ingersoll & Rooney PC

(57) ABSTRACT

A gas treatment apparatus for treating a gas by bringing the gas into contact with a treatment liquid. The gas treatment apparatus includes a gas-liquid contact chamber for a gas-liquid contact of the gas with the treatment liquid, a storage chamber, located over the gas-liquid contact chamber, for storing the treatment liquid, and a treatment liquid supplying unit for supplying the treatment liquid stored in the storage chamber to an inside of the gas-liquid contact chamber with a gravity-drop.

4 Claims, 4 Drawing Sheets

U.S. PATENT DOCUMENTS

| | | | |
|---|---|---|---|
| 5,939,020 | A | 8/1999 | Glaunsinger et al. |
| 5,980,845 | A * | 11/1999 | Cherry ................... 423/229 |
| 6,977,066 | B1 | 12/2005 | Iwanaga et al. |
| 2004/0024244 | A1 | 2/2004 | Walsdorff et al. |
| 2005/0046052 | A1 * | 3/2005 | Okada et al. ............ 261/115 |
| 2006/0099138 | A1 | 5/2006 | Walsdorff et al. |
| 2006/0123842 | A1 | 6/2006 | Sohn et al. |
| 2007/0232827 | A1 | 10/2007 | Wolfert et al. |
| 2008/0138252 | A1 | 6/2008 | Sasaki et al. |

FOREIGN PATENT DOCUMENTS

| | | | |
|---|---|---|---|
| JP | 59-173101 | A | 10/1984 |
| JP | 62-275001 | A | 11/1987 |
| JP | 06-319946 | A | 11/1994 |
| JP | 09075916 | A * | 3/1997 |
| JP | 2000-272906 | A | 10/2000 |
| JP | 2001-019405 | A | 1/2001 |
| JP | 2001-516333 | A | 9/2001 |
| JP | 2002-136828 | A | 5/2002 |
| WO | WO 97/24320 | A1 | 7/1997 |
| WO | WO 2004/014845 | A1 | 2/2004 |
| WO | WO 2004/037718 | A2 | 5/2004 |
| WO | WO 2004/056758 | A1 | 7/2004 |

OTHER PUBLICATIONS

English translation of JP 55-047117 A, which was published Apr. 3, 1980.*

International Preliminary Report on Patentability and Written Opinion issued in corresponding International Patent Application No. PCT/JP2006/305344; Oct. 18, 2007; The International Bureau of WIPO, Geneva, CH.

First and Second Notice Informing the Applicant of the Communication of the International Application issued in corresponding International Patent Application No. PCT/JP2006/305344; Nov. 9, 2006 and Aug. 9, 2007; The International Bureau of WIPO, Geneva, CH.

Official Action dated Feb. 1, 2011, issued in corresponding Japanese Patent Application No. 2005-103945.

* cited by examiner

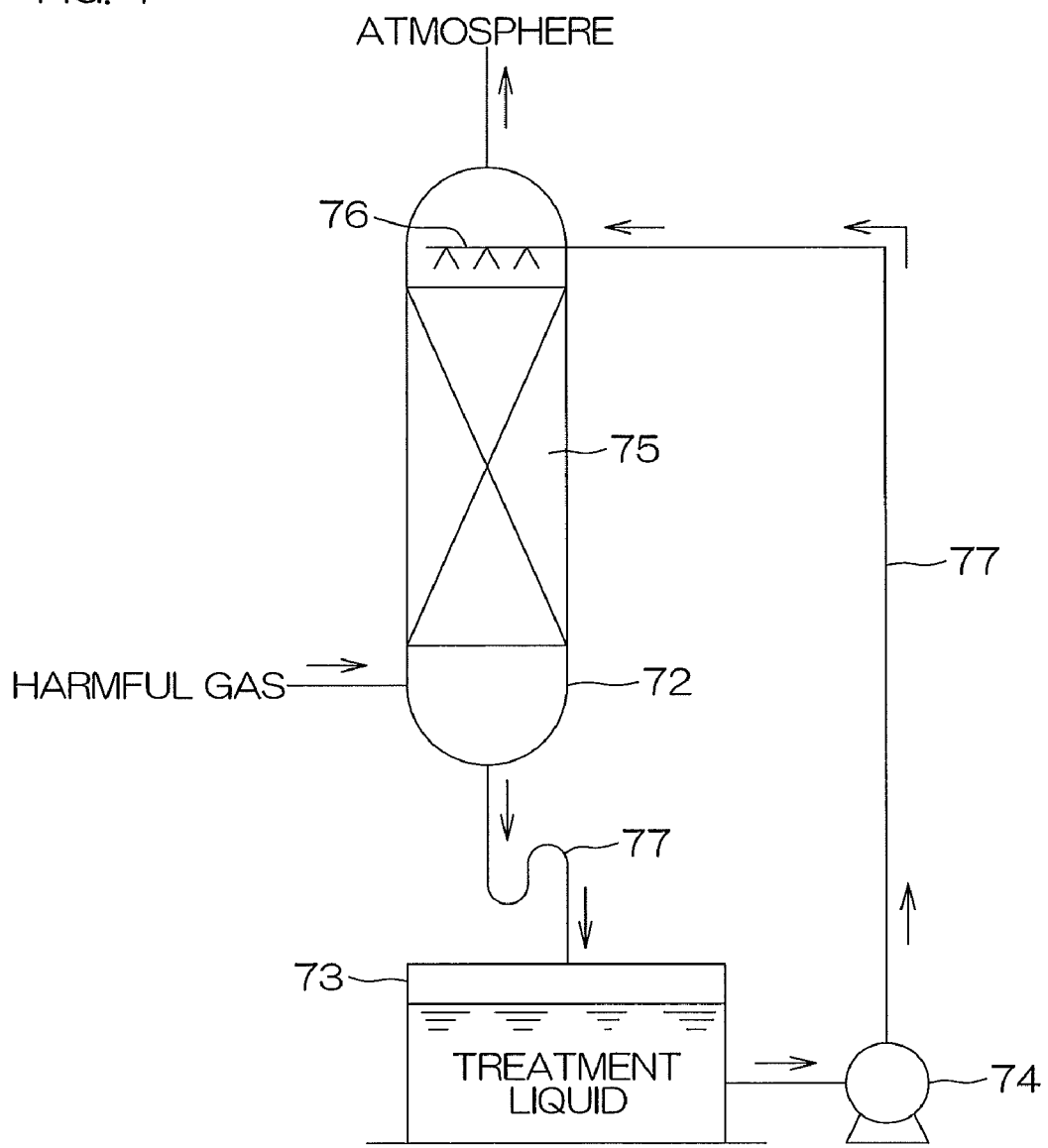

POLYISOCYANATE PRODUCTION SYSTEM AND GAS TREATMENT APPARATUS

CROSS-REFERENCE TO RELATED APPLICATIONS

This application is a divisional of U.S. application Ser. No. 11/597,756 filed on Nov. 28, 2006, which is a U.S. national stage application of International Application No. PCT/JP2006/305344 filed on Mar. 17, 2006 and which claims priority to Japanese Application Nos. 2005-108592 and 2005-108593, both filed on Apr. 5, 2005, the entire contents of which are incorporated herein by reference.

TECHNICAL FIELD

The present invention relates to a polyisocyanate production system for producing polyisocyanate used as a raw material of polyurethane, and to a gas treatment apparatus for treating gas by bringing the gas into contact with a treatment liquid.

BACKGROUND ART

Polyisocyanate used as a raw material of polyurethane is industrially produced by reacting carbonyl chloride with polyamine for isocyanate reaction.

In this isocyanate reaction, corresponding polyisocyanate is produced from polyamine and hydrochloric gas is produced secondarily.

A production method for producing chlorine industrially by oxidizing the hydrochloric gas thus produced secondarily is known (cf. Patent Documents 1 and 2 listed below, for example).

A plant for manufacturing chemicals is provided with a gas treatment apparatus for detoxifying e.g. a harmful gas produced in a chemical process. This gas treatment apparatus comprises, for example, a filling column, a spray column, and a scrubber, and the one used for treating the harmful gas is sometimes called a detoxification column.

A detoxification column shown in FIG. 4 is known as an example of the gas treatment apparatus (cf. Patent Document 3 list below, for example).

This detoxification column 71 includes a treatment tank 72, a storage tank 73, and a pump 74. The treatment tank 72 has a gas-liquid contact chamber 75 in which a packed material is packed to improve efficiency of gas-liquid contact and also has showers 76 arranged over the gas-liquid contact chamber 75. A bottom of the treatment tank 72, the storage tank 73, the pump 74, and the showers 76 are connected via a circulation line 77.

A treatment liquid for detoxifying the harmful gas is stored in the storage tank 73. The treatment liquid is circulated in the following sequence: The treatment liquid is first pumped up by the pump 74 upward through the circulation line 77, then, sprayed from the showers 76 into the gas-liquid contact chamber 75 of the treatment tank 72. After passing through the gas-liquid contact chamber 75, the treatment liquid flows back to the storage tank 73 from the bottom of the treatment tank 72.

On the other hand, a harmful gas is supplied to the treatment tank 72 in such a manner as to flow upward from the bottom of the gas-liquid contact chamber 75 so that the harmful gas contacts the treatment liquid sprayed from the showers 76 in the vertically opposite direction for an effective gas-liquid contact, so that the harmful gas is detoxified. Then, the resultant gas is discharged from the treatment tank 72 to the atmosphere.

In Patent Document 3 listed below, a carbonyl-chloride-containing gas as the harmful gas is detoxified by this detoxification column using a sodium hydroxide liquid solution as the treatment liquid.

Document 1: Japanese Laid-open (Unexamined) Patent Publication No. Sho 62-275001,
Patent Document 2: Japanese Laid-open (Unexamined) Patent Publication No. 2000-272906, and
Patent Document 3: Japanese Laid-open (Unexamined) Patent Publication No. Hei 6-319946.

DISCLOSURE OF THE INVENTION

Problem to be Solved by the Invention

When a production of polyisocyanate is attempted by the process that carbonyl chloride and polyamine undergo isocyanate reaction; the hydrochloric gas produced secondarily in the isocyanate reaction is oxidized by oxygen to thereby produce chlorine; the chlorine obtained and carbon monoxide are reacted to produce carbonyl chloride; and then the carbonyl chloride obtained with the polyamine undergoes the isocyanate reaction, it is found that when the isocyanate reaction varies for various reasons, an amount of hydrochloric gas produced secondarily may vary. Then, when the amount of hydrochloric gas produced secondarily varies, an amount of hydrochloric gas supplied in the oxidation process of oxidizing the hydrochloric gas varies.

To ensure an industrially steady production of chlorine, steady supply of hydrochloric gas produced secondarily to a hydrochloric gas oxidation tank is required.

Also, to ensure a stable reaction between carbonyl chloride and polyamine in an isocyanate producing reactor, an inner pressure of the isocyanate producing reactor must be kept constant.

Accordingly it is desired that even with variations of hydrochloric gas produced secondarily from the isocyanate reaction, the hydrochloric gas is treated effectively in consideration of these two factors described above.

In addition, when a trouble occurs in the hydrochloric gas oxidation tank for oxidizing the hydrochloric gas produced secondarily, the treatment of the hydrochloric gas produced secondarily is troubled.

Further, when a trouble occurs, for example, in the pump 74 of the detoxification column 71, the treatment liquid through the circulation line 77 is not circulated. As a result of this, the efficiency of the gas-liquid contact of the harmful gas with the treatment liquid in the treatment tank 72 is reduced. Furthermore, when the pumping of the treatment liquid is interrupted, the treatment liquid remaining in the gas-liquid contact chamber 75 may be consumed to cause a possible problem that the harmful gas cannot be detoxified.

It is an object of the present invention to provide a polyisocyanate production system that can stably produce chlorine from hydrogen chloride produced secondarily while ensuring stable reaction between carbonyl chloride and polyamine and can also provide effective treatment of the hydrochloric gas produced secondarily.

It is another object of the present invention to provide a polyisocyanate production system that can provide effective treatment of the hydrogen chloride even when a trouble occurs in a chorine production unit for producing chlorine from the hydrogen chloride produced secondarily.

It is a further another object of the present invention to provide a gas treatment apparatus that can supply a treatment liquid to the inside of a gas-liquid contact chamber without any need of particular power source.

Means for Solving the Problem

The present invention provides a polyisocyanate production system comprising a polyisocyanate producing unit for producing polyisocyanate by reacting carbonyl chloride with polyamine, a hydrogen chloride purifying unit to which hydrogen chloride produced secondarily in the polyisocyanate producing unit is supplied to purify hydrogen chloride, a chlorine producing unit to which the hydrogen chloride purified in the hydrogen chloride purifying unit is supplied and in which the hydrogen chloride is oxidized to produce the chlorine, a hydrochloric acid producing unit to which the hydrogen chloride purified in the hydrogen chloride purifying unit is supplied and in which the hydrogen chloride is absorbed in water to produce a hydrochloric acid, a first adjusting unit for adjusting an amount of hydrogen chloride supplied from the hydrogen chloride purifying unit to the hydrochloric acid producing unit, a second adjusting unit for adjusting an amount of hydrogen chloride supplied from the hydrogen chloride purifying unit to the chlorine producing unit, and a control unit for controlling the second adjusting unit so that an amount of hydrogen chloride supplied from the hydrogen chloride purifying unit to the chlorine producing unit is kept constant and controlling the first adjusting unit so that an inner pressure of the hydrogen chloride purifying unit is constant.

According to this polyisocyanate production system, the control unit controls the second adjusting unit to keep an amount of hydrogen chloride supplied from the hydrogen chloride purifying unit to the chlorine producing unit to be constant and also controls the first adjusting unit to adjust an amount of hydrogen chloride supplied from the hydrogen chloride purifying unit to the chlorine producing unit, so as to keep a pressure of an inside of the hydrogen chloride purifying unit constant. This provides the result that the hydrogen chloride can be steadily supplied to the chlorine producing unit, while the pressure of the inside of the hydrogen chloride purifying unit can be kept constant by supplying surplus hydrogen chloride to the hydrochloric acid producing unit from the hydrogen chloride purifying unit.

As a result of this, chlorine can be steadily produced from the hydrogen chloride produced secondarily, while the inner pressure of the hydrogen chloride purifying unit and thus the pressure of the inside of the polyisocyanate producing unit can be kept constant. This ensures a stable reaction between carbonyl chloride and polyamine and enables an effective treatment of the hydrochloric gas produced secondarily.

In this polyisocyanate production system, it is preferable that unoxidized hydrogen chloride and hydrochloric acid in the chlorine producing unit are supplied to the hydrochloric acid producing unit.

When unoxidized hydrogen chloride in the chlorine producing unit and hydrochloric acid produced in the chlorine producing unit are supplied to the hydrochloric acid producing unit without being discharged, the hydrochloric acid can be produced more effectively for effective utilization of the surplus hydrogen chloride.

In this polyisocyanate production system, it is preferable that the hydrochloric acid producing unit is provided with a hydrochloric-acid-concentration adjusting unit for adjusting a concentration of the hydrochloric acid produced.

When a concentration of the hydrochloric acid produced is adjusted by the hydrochloric-acid-concentration adjusting unit, a hydrochloric acid of stable quality can be produced.

Further, the present invention provides a polyisocyanate production system comprising a polyisocyanate producing unit for producing polyisocyanate by reacting carbonyl chloride with polyamine, a hydrogen chloride purifying unit, connected to the polyisocyanate producing unit for purifying the hydrogen chloride produced secondarily in the polyisocyanate producing unit, a chlorine producing unit connected to the hydrogen chloride purifying unit for producing chlorine by oxidizing the hydrogen chloride purified in the hydrogen chloride purifying unit, a first detoxifying treatment unit connected to the hydrogen chloride purifying unit in parallel with respect to the chlorine producing unit, for detoxifying the hydrogen chloride discharged from the hydrogen chloride purifying unit, a second detoxifying treatment unit selectively connected to the hydrogen chloride purifying unit with respect to the chlorine producing unit, for detoxifying the hydrogen chloride discharged from the hydrogen chloride purifying unit, an abnormality detecting unit for detecting an abnormality of the hydrogen chloride purifying unit, and a connection switching unit which connects the chlorine producing unit with the hydrogen chloride purifying unit when an abnormality is not detected by the abnormality detecting unit and connects the second detoxifying treatment unit with the hydrogen chloride purifying unit when an abnormality is detected by the abnormality detecting unit.

According to this polyisocyanate production system, when an abnormality of the hydrogen chloride purifying unit is not detected by the abnormality detecting unit, the hydrogen chloride purified by the hydrogen chloride purifying unit is supplied to the chlorine producing unit to produce chlorine from the hydrogen chloride supplied in the chlorine producing unit and is discharged to the first detoxifying treatment unit to detoxify the hydrogen chloride supplied in the first treatment unit.

On the other hand, when following an abnormality being in the chlorine producing unit, an abnormality of the hydrogen chloride purifying unit is detected by the abnormality detecting unit, the connection switching unit switches the connection between the hydrogen chloride purifying unit and the chlorine producing unit to the connection between the hydrogen chloride purifying unit and the second detoxifying treatment unit according to a treating capability of the first detoxifying treatment unit. Then, the hydrogen chloride supplied to the chlorine producing unit in the interim is discharged to the second detoxifying treatment unit to detoxify the hydrogen chloride by the second detoxifying treatment unit.

As a result of this, when the chlorine producing unit is normal, the hydrogen chloride is steadily supplied to the chlorine producing unit, while surplus hydrogen chloride is detoxified in the first detoxifying treatment unit. On the other hand, when a trouble occurs in the chlorine producing unit, the hydrogen chloride supplied to the chlorine producing unit in the interim is detoxified in the second detoxifying treatment unit depending on an amount of the surplus hydrogen chloride which exceeds a treating capability of the first detoxifying treatment unit. This can achieve an effective treatment of the hydrogen chloride.

In this polyisocyanate production system, it is preferable that the connection switching unit comprises a first opening and closing unit for connecting the chlorine producing unit to connect to or disconnect from the hydrogen chloride purifying unit, a second opening and closing unit for connecting the second detoxifying treatment unit to or disconnecting from the hydrogen chloride purifying unit, and a control unit for controlling the first opening and closing unit and the second opening and closing unit, wherein when an abnormality is not detected by the abnormality detecting unit, the control unit controls the first opening and closing unit to connect the chlorine producing unit with the hydrogen chloride purifying unit and also controls the second opening and closing unit to disconnect the second detoxifying treatment unit from the hydrogen chloride purifying unit, while on the other hand, when an abnormality is detected by the abnormality detecting unit, the control unit controls the first opening and closing unit to disconnect the chlorine producing unit from the hydrogen chloride purifying unit or to reduce the hydrogen chloride purified in the hydrogen chloride purifying unit rapidly in amount supplied to the chlorine producing unit and also controls the second opening and closing unit to connect the second detoxifying treatment unit with the hydrogen chloride purifying unit according to a treating capability of the first detoxifying treatment unit.

According to this polyisocyanate production system, when an abnormality is not detected by the abnormality detecting unit, the control unit controls the first opening and closing unit to connect the chlorine producing unit with the hydrogen chloride purifying unit and also controls the second opening and closing unit to disconnect the second detoxifying treatment unit from the hydrogen chloride purifying unit, while on the other hand, when an abnormality is detected by the abnormality detecting unit, the control unit controls the first opening and closing unit to disconnect the chlorine producing unit from the hydrogen chloride purifying unit or to reduce the hydrogen chloride purified in the hydrogen chloride purifying unit rapidly in an amount supplied to the chlorine producing unit and also controls the second opening and closing unit to connect the second detoxifying treatment unit with the hydrogen chloride purifying unit according to a treating capability of the first detoxifying treatment unit. This provides the result that when a trouble occurs in the chlorine producing unit, hydrogen chloride supplied to the chlorine producing unit in the interim is surely discharged to the second detoxifying treatment unit to be detoxified depending on an amount of the surplus hydrogen chloride which exceeds a treating capability of the first detoxifying treatment unit.

In this polyisocyanate production system, it is preferable that the first detoxifying treatment unit is a hydrochloric acid producing unit for producing hydrochloric acid by absorbing the hydrogen chloride in water.

When the first detoxifying treatment unit comprises a hydrochloric acid producing unit, surplus hydrogen chloride can be detoxified, while hydrochloric acid can be produced from the surplus hydrogen chloride for recycling purpose. This produces the result that an effective utilization of the surplus hydrogen chloride can be made.

In this polyisocyanate production system, it is preferable that the unoxidized hydrogen chloride and the hydrochloric acid in the chlorine producing unit are supplied to the hydrochloric acid producing unit.

When the unoxidized hydrogen chloride in the chlorine producing unit or the hydrochloric acid produced in the chlorine producing unit is supplied to the hydrochloric acid producing unit without being discharged therefrom, hydrochloric acid can be produced more effectively, thus providing the result that an effective utilization of surplus hydrogen chloride can be made.

It is preferable that this polyisocyanate production system comprises a first adjusting unit for adjusting an amount of hydrogen chloride supplied from the hydrogen chloride purifying unit to the hydrochloric acid producing unit, a second adjusting unit for adjusting an amount of hydrogen chloride supplied from the hydrogen chloride purifying unit to the chlorine producing unit, and a control unit for controlling the second adjusting unit so that an amount of hydrogen chloride supplied from the hydrogen chloride purifying unit to the chlorine producing unit is kept constant and controlling the first adjusting unit so that an inner pressure of the hydrogen chloride purifying unit is kept constant.

When the control unit controls the second adjusting unit so that an amount of hydrogen chloride supplied from the hydrogen chloride purifying unit to the chlorine producing unit is kept constant and controls the first adjusting unit to adjust an amount of hydrogen chloride supplied from the hydrogen chloride purifying unit to the chlorine producing unit so as to keep the inner pressure of the hydrogen chloride purifying unit constant, the hydrogen chloride can be steadily supplied to the chlorine producing unit, while surplus hydrogen chloride is supplied from the hydrogen chloride purifying unit to the hydrochloric acid producing unit, whereby the inner pressure of the hydrogen chloride purifying unit is kept constant.

This produces the result that the chlorine can be steadily produced from the hydrogen chloride produced secondarily, while the inner pressure of the hydrogen chloride purifying unit and thus the inner pressure of the polyisocyanate producing unit can be kept constant. This allows a stable reaction between carbonyl chloride and polyamine to ensure an effective treatment of the hydrogen chloride produced secondarily.

Further, the present invention provides a gas treatment apparatus for treating a gas by bringing the gas into contact with a treatment liquid, which comprises a gas-liquid contact chamber for a gas-liquid contact between the gas and the treatment liquid, a storage chamber, located over the gas-liquid contact chamber, for storing the treatment liquid, and a treatment liquid supplying unit for supplying the treatment liquid stored in the storage chamber to an inside of the gas-liquid contact chamber via a gravity-drop.

According to this gas treatment apparatus, the treatment liquid is supplied with a gravity drop from the storage chamber located over the gas-liquid contact chamber to the interior of the gas-liquid contact chamber by the treatment liquid supplying unit without any specific power source. Even when some trouble occurs in the power source used for supplying the treatment liquid to the storage chamber, the treatment liquid is steadily supplied to the interior of the gas-liquid contact chamber by the treatment liquid supplying unit until the treatment liquid in the storage tank runs out.

As a result of this, even when the supply of the treatment liquid to the gas-liquid contact chamber is interrupted due to some trouble in the power source, the gas-liquid contact between the treatment liquid and the gas in the gas-liquid contact chamber can be continued and also the treatment of the gas can be continued, thus providing further improvement in safety.

Preferably, the gas treatment apparatus of the present invention comprises a plurality of the gas-liquid contact chambers, and a gas passage path for passing the gas in series through the respective gas-liquid contact chambers, and the treatment liquid supplying unit supplies the treatment liquid to the gas-liquid contact chamber located at least at a most downstream side with respect to a flowing direction of the gas flowing along the gas passage path.

When there are provided a plurality of gas-liquid contact chambers and the gas passage path for passing the gas in series through those gas-liquid contact chambers, a treatment of the gas can be carried out multistage-wise and continuously, thus achieving an effective treatment of the gas.

Further, since the treatment liquid supplying unit supplies the treatment liquid at least to the gas-liquid contact chamber located at a most downstream side with respect to a flowing direction of the gas flowing along the gas passage path even with providing of the plurality of gas-liquid contact chambers, even when the supply of the treatment liquid to the gas-liquid contact chambers is interrupted due to some trouble in the power source, the gas-liquid contact between the treatment liquid and the gas can be continued at least in the gas-liquid contact chamber located at the most downstream side, thus providing a further improvement in safety.

Preferably, the gas treatment apparatus of the present invention further comprises a treatment liquid back-flow unit for returning the treatment liquid discharged from the gas-liquid contact chamber to the storage chamber.

When the treatment liquid returns via the treatment liquid back-flow unit, a waste of the treatment liquid can be minimized and running costs can be reduced.

The gas treatment apparatus of the present invention is preferably used as a gas treatment apparatus for detoxifying the carbonyl-chloride-containing gas in which the gas is a carbonyl-chloride-containing gas, and the treatment liquid is an alkaline aqueous solution.

Also, the gas treatment apparatus of the present invention is preferably used as a gas treatment apparatus using a hydrogen-chloride-containing gas as the gas and water or alkaline aqueous solution as the treatment liquid used for detoxifying the hydrogen-chloride-containing gas.

Further, the gas treatment apparatus of the present invention is preferably used as a gas treatment apparatus using a combination of ammonia- or alkylamine-containing gas and water or an acid aqueous solution; a Sox- or NOx-containing gas and water or an alkaline aqueous solution; a volatile-organic-compound-containing gas and an organic solvent, etc. as a combination of the gas and the treatment liquid, for removal (detoxification), absorption and collection of the gas.

Effect of the Invention

According to the polyisocyanate production system of the present invention, chlorine can be steadily produced from hydrogen chloride produced secondarily, while the inner pressure of the polyisocyanate producing unit can be kept constant. This ensures a stable reaction between carbonyl chloride and polyamine and an effective treatment of the hydrochloric gas produced secondarily.

According to the polyisocyanate production system of the present invention, when the chlorine producing unit is normal, the hydrogen chloride is steadily supplied to the chlorine producing unit, while surplus hydrogen chloride is detoxified in the first detoxifying treatment unit. On the other hand, when some trouble occurs in the chlorine producing unit, the hydrogen chloride supplied to the chlorine producing unit in the interim is detoxified in the second detoxifying treatment unit depending on an amount of the surplus hydrogen chloride which exceeds a treating capability of the first detoxifying treatment unit. This provides the result that regardless of the treating capability of the first detoxifying treatment unit, the hydrogen chloride can be detoxified, thus achieving an effective treatment of the hydrogen chloride.

According to the polyisocyanate production system of the present invention, even when the supply of the treatment liquid to the gas-liquid contact chamber is interrupted due to some trouble in the power source, the gas-liquid contact between the treatment liquid and the gas in the gas-liquid contact chamber can be continued and the treatment of the gas can be continued, thus providing a further improvement in safety.

BRIEF DESCRIPTION OF THE DRAWINGS

FIG. 4 is a schematic block diagram showing a conventional type of detoxification column disclosed in a known literature.

EXPLANATION OF LETTERS OR NUMERALS

Figure 1:
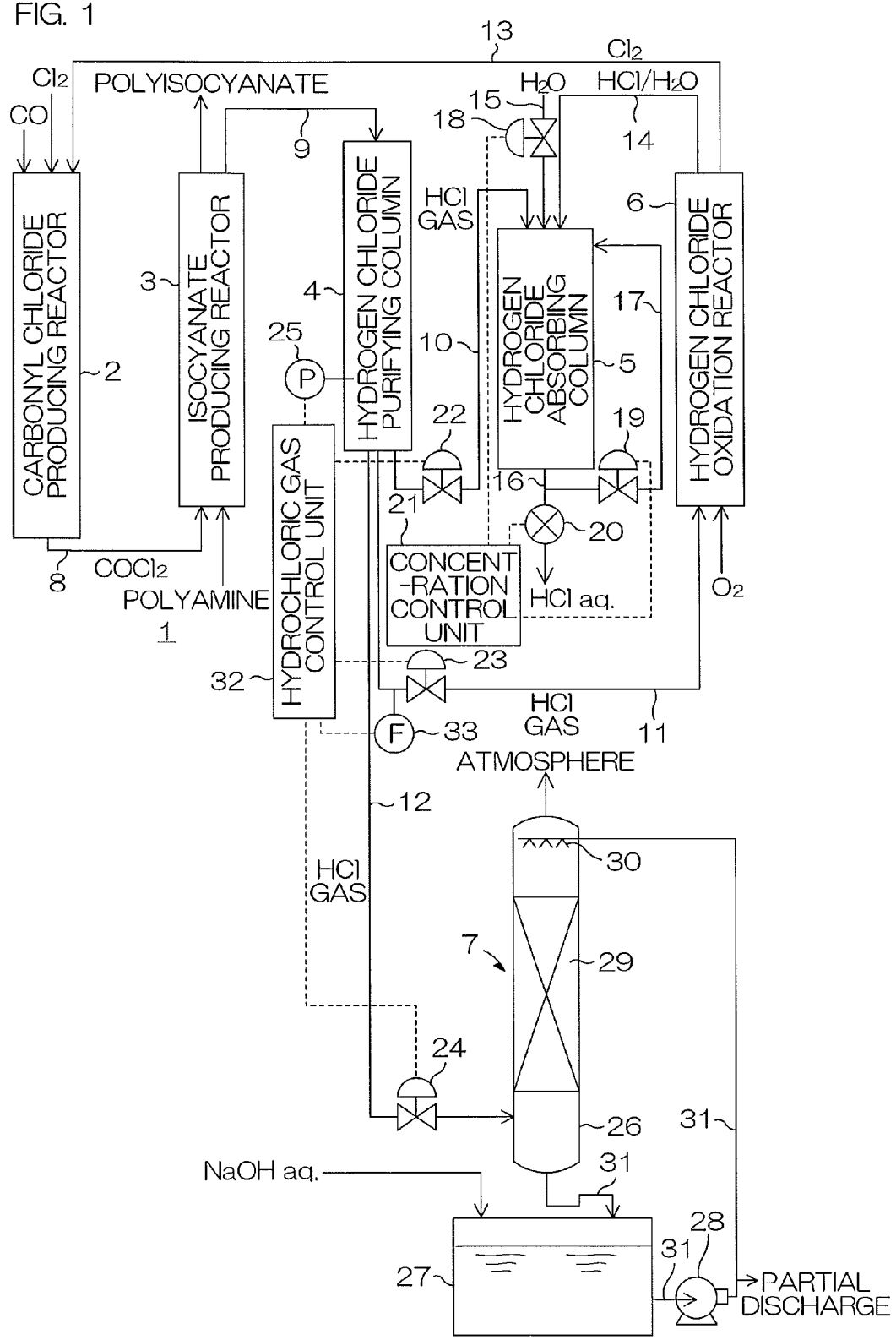
FIG. 1 is a schematic block diagram showing an embodiment of a polyisocyanate production system of the present invention.

1: Polyisocyanate production system
3: Isocyanate producing reactor
4: Hydrogen chloride purifying tank
5: Hydrogen chloride absorbing column
6: Hydrogen chloride oxidation reactor
7: Detoxification column
21: Concentration control unit
22: Pressure control valve
23: Flow-rate control valve
24: Valve
25: Pressure sensor
32: Hydrochloric gas control unit
51: Detoxification column
55: Gas-liquid contact chamber
56: Storage chamber
57: Treatment liquid supply pipe
61: Harmful gas charge pipe
62: Treated gas discharge pipe
63: Back-flow pipe
64: Transport pipe

EMBODIMENTS OF THE INVENTION

FIG. 1 is a schematic block diagram showing an embodiment of a polyisocyanate production system of the present invention.

As shown in FIG. 1, a polyisocyanate production system 1 comprises a carbonyl chloride producing reactor 2, an isocyanate producing reactor 3 serving as a polyisocyanate producing unit, a hydrogen chloride purifying tank 4 serving as a hydrogen chloride purifying unit, a hydrogen chloride absorbing column 5 serving as a first detoxifying treatment unit and a hydrochloric acid producing unit, a hydrogen chloride oxidation reactor 6 serving as a chlorine producing unit, and a detoxification column 7 serving as a second detoxifying treatment unit.

The carbonyl chloride producing reactor 2 is not limited to any particular one as long as it is a reactor for a reaction of chlorine ($Cl_2$) with carbon monoxide (CO) to produce carbonyl chloride ($COCl_2$). For example, the carbonyl chloride producing reactor 2 includes a fixed bed reactor in which an activated carbon catalyst is packed. The carbonyl chloride producing reactor 2 is connected to an isocyanate producing reactor 3 via a connection line 8.

Chlorine gas and carbon monoxide gas, which are raw materials of carbonyl chloride, are supplied to the carbonyl chloride producing reactor 2 in such a proportion that a ratio (molar ratio) of carbon monoxide to chlorine is 1.01/1-10/1. When chlorine is oversupplied, there is a possibility that an aromatic ring of polyisocyanate and a hydrocarbon group may be chlorinated in the isocyanate producing reactor 3 by the oversupplied chlorine.

An amount of chlorine gas supplied and an amount of carbon monoxide supplied are properly determined on the basis of an amount of polyisocyanate produced and an amount of hydrogen chloride gas produced secondarily.

In the carbonyl chloride producing reactor 2, chlorine and carbon monoxide are reacted with each other to produce carbonyl chloride. In this reaction, the carbonyl chloride producing reactor 2 is set at 0-250° C. and 0-5 MPa-gauge, for example.

The carbonyl chloride obtained may be cooled and liquefied properly to be in a liquefied state in the carbonyl chloride producing reactor 2 or may be absorbed properly in an adequate solvent to be a solution. The carbonyl chloride obtained is re-supplied to the carbonyl chloride producing reactor 2 according to need, after the carbon monoxide therein is removed.

When at least a part of carbonyl chloride is in a liquefied state and/or solution state, a concentration of carbon monoxide contained in the carbonyl chloride can be reduced. This can provide an improved conversion ratio of hydrochloric gas to chlorine in an oxidation reaction of hydrogen chloride mentioned later.

For producing liquefied carbonyl chloride, a condenser is provided in the carbonyl chloride producing reactor 2 at a portion thereof on the downstream side of the fixed bed reactor mentioned above, so that the carbonyl chloride obtained can be liquefied by that condenser. For this liquefying process, it is preferable that a concentration of carbon monoxide contained in the carbonyl chloride is 1% by weight or less.

Then, the carbonyl chloride thus obtained is supplied to the isocyanate producing reactor 3 via the connection line 8.

The isocyanate producing reactor 3 is not limited to any particular one, as long as it is a reaction tank for a reaction of carbonyl chloride with polyamine to produce polyisocyanate. The isocyanate producing reactor 3 includes a reactor provided with a stirring vane and a reaction column having a perforated plate. Preferably, the isocyanate producing reactor 3 is configured as a multistage tank. An adequate solvent or gas inactive to polyisocyanate is used for the isocyanate reaction. The isocyanate producing reactor 3 is connected to the hydrogen chloride purifying tank 4 through the connection line 9.

As raw materials, carbonyl chloride and polyamine are supplied from the carbonyl chloride producing reactor 2 to the isocyanate producing reactor 3 through the connection line 8.

The carbonyl chloride is supplied from the carbonyl chloride producing reactor 2 in the condition of a gaseous state or in the condition of a liquefied and/or solution state in such a proportion that a ratio (molar ratio) of carbonyl chloride to polyamine is 2/1-60/1.

The polyamine used is a polyamine corresponding to a polyisocyanate used in a production of polyurethane. No particular limitation is imposed on the polyamine. For example, the polyamine is properly selected from aromatic diamines, such as polymethylenepolyphenylene polyamine (MDA) corresponding to polymethylenepolyphenylene polyisocyanate (MDI) and tolylenediamine (TDA) corresponding to tolylene diisocyanate (TDI), aralkyl diamines, such as xylylenediamine (XDA) corresponding to xylylenediisocyanate (XDI) and tetramethylxylylene diamine (TMXDA) corresponding to tetramethylxylylene diisocyanate (TMXDI), alicyclic diamines, such as bis(aminomethyl) norbornane (NBDA) corresponding to bis(isocyanatomethyl) norbornane (NBDI), 3-aminomethyl-3,5,5-trimethylcyclohexyl amine (IPDA) corresponding to 3-isocyanatomethyl-3,5,5-trimethylcyclohexyl isocyanate (IPDI), 4,4'-methylenebis(cyclohexylamine) ($H_{12}$MDA) corresponding to 4,4'-methylenebis (cyclohexylisocyanate) ($H_{12}$MDI), and bis(aminomethyl) cyclohexane ($H_6$XDA) corresponding to bis(isocyanatomethyl)cyclohexane ($H_6$XDI), aliphatic diamines, such as hexamethylene diamine (HDA) corresponding to hexamethylene diisocyanate (HDI), and polymethylenepolyphenyl polyamine corresponding to polymethylenepolyphenyl polyisocyanate (crude MDI, polymeric MDI).

The polyisocyanate production system 1 is suitable for producing aromatic diisocyanate and polymethylenepolyphenyl polyisocyanate from aromatic diamine and polymethylene polyphenyl polyamine.

Although the polyamine may be supplied directly, it is preferable that the polyamine is dissolved in a solvent to be a solution of 5 to 50% by weight.

The solvent used is not limited to any particular one. The solvents that may be used include the following: aromatic hydrocarbons such as toluene and xylene; halogenated hydrocarbons such as chlorotoluene, chlorobenzene and dichlorobenzene; esters such as butyl acetate and amyl acetate, and ketones such as methylisobutyl ketone and methylethyl ketone. Preferably, chlorobenzene and dichlorobenzene can be cited.

In the isocyanate producing reactor 3, the carbonyl chloride and the polyamine undergo an isocyanate reaction to produce polyisocyanate, while hydrochloric gas (HCl gas) is also produced secondarily. In the isocyanate reaction, the above-mentioned solvent is added in the isocyanate producing reactor 3 separately or together with polyamine in the isocyanate producing reactor 3 and the isocyanate producing reactor 3 is set at 0-250° C. and 0-5 MPa-gauge, for example.

The polyisocyanate undergoes an aftertreatment such as degasification, desolvating, and tar cutting, then is purified and provided as a raw material of polyurethane.

The hydrochloric gas produced secondarily is supplied to the hydrogen chloride purifying tank 4 via the connection line 7, together with an entrained solvent and carbonyl chloride The hydrogen chloride purifying tank 4 is not limited to any particular one as long as it can purify the hydrochloric gas by separating the entrained solvent and carbonyl chloride therefrom. For example, the hydrogen chloride purifying tank 4 includes a tray column and a packed column which are provided with a condenser.

The hydrogen chloride purifying tank 4 is connected to the hydrogen chloride absorbing column 5 through a first hydrochloric gas connection line 10. Also, the hydrogen chloride purifying tank 4 is connected to the hydrogen chloride oxidation reactor 6 through a second hydrochloric gas connection line 11. Further, the hydrogen chloride purifying tank 4 is connected to the detoxification column 7 through a third hydrochloric gas connection line 12.

A pressure control valve 22 serving as a first adjusting unit for adjusting an amount of hydrochloric gas supplied is interposed in the first hydrochloric gas connection line 10 via which the hydrochloric gas is supplied from the hydrogen chloride purifying tank 4 to the hydrogen chloride absorbing column 5. Also, a flow-rate control valve 23 serving as a second adjusting unit of the first opening and closing unit for adjusting an amount of hydrochloric gas supplied is interposed in the second hydrochloric gas connection line 11 via which the hydrochloric gas is supplied from the hydrogen chloride purifying tank 4 to the hydrogen chloride absorbing column 5. Also, a valve 24 serving as a second opening and closing unit is interposed in the third hydrochloric gas connection line 12 via which the hydrochloric gas is supplied from the hydrogen chloride purifying tank 4 to the detoxification column 7. A flowmeter 33 is interposed in the third hydrochloric gas connection line 12 at a location on the upstream side of the valve 24. A pressure sensor 25 serving as an abnormality detecting unit for detecting the inner pressure of the tower is provided in the hydrogen chloride purifying tank 4, so that the inner pressure of the tank is kept at e.g. 0.05-0.6 MPa.

The pressure control valve 22, the flow-rate-control valve 23, the valve 24, the flowmeter 33, and the pressure sensor 25 are connected to a hydrochloric gas control unit 32 serving as a control unit. A connection switching unit is composed by the flow-rate-control valve 23, the valve 24, and the hydrochloric gas control unit 32. The inner pressure of the hydrochloric gas purifying tank 4 detected by the pressure sensor 25 is input to the hydrochloric gas control unit 32.

When the inner pressure of the hydrochloric gas purifying tank 4 detected by the pressure sensor 25 is not more than a predetermined level (e.g. 0.6 MPa), the hydrochloric gas control unit 32 regards the hydrogen chloride oxidation reactor 6 as normal and controls the flow-rate control valve 23 to connect the hydrogen chloride oxidation reactor 6 to the hydrogen chloride purifying tank 4 and also controls the valve 24 to disconnect the detoxification column 7 from the hydrogen chloride purifying tank 4. On the other hand, due to an abnormality of the hydrogen chloride oxidation reactor 6, the flow-rate control valve 23 is shutoff or an opening of the flow-rate control valve 23 is reduced rapidly, to reduce a flow-rate of the flowmeter 33 rapidly. In this case, when an amount of hydrochloric gas produced secondarily from the isocyanate producing reactor 3 exceeds the treating capability of the hydrogen chloride absorbing column 5 so that the inner pressure of the hydrochloric gas purifying tank 4 exceeds a predetermined level (e.g. 0.6 MPa) accordingly, the hydrochloric gas control unit 32 controls the valve 24 to connect the detoxification column 7 to the hydrogen chloride purifying tank 4.

In the hydrogen chloride purifying tank 4, the carbonyl chloride is condensed by the condenser or absorbed by the solvent, so as to be separated from the hydrochloric gas, and also a little amount of a solvent in the hydrochloric gas is separated from the hydrochloric gas by being absorbed in an activated carbon and the like.

In the hydrogen chloride purifying tank 4, a concentration of an organic material in the hydrochloric gas is preferably reduced to be 1% by weight or less, or preferably 100 ppm or less, and a concentration of carbon monoxide in the hydrochloric gas is preferably reduced to be 10% (V/V) (percent by volume) or less, or preferably 3% (V/V) or less. By reducing impurities in the hydrochloric gas to such a low level, disadvantageous effects on the catalyst, such as a decreased activity or a partial deactivation of the catalyst, can be reduced or prevented in the hydrogen chloride oxidation reaction mentioned later. This can achieve an improved basic unit, an improved oxidation reaction of the hydrogen chloride, and an equalized temperature distribution of the hydrogen chloride oxidation reactor 6 to stabilize the hydrogen chloride oxidation reactor 6. Further, this can improve a conversion ratio of hydrochloric gas to chlorine.

Since the hydrogen chloride oxidation reactor 6 and the hydrogen chloride absorbing column 5 are connected in parallel to the hydrogen chloride purifying tank 4, when the hydrogen chloride oxidation reactor 6 is in normal, the most of the purified hydrochloric gas is supplied the hydrogen chloride oxidation reactor 6 via the second hydrochloric gas connection line 11 and a surplus of the purified hydrochloric gas is discharged to the hydrogen chloride absorbing column 5. A proportion between the hydrochloric gas supplied to the hydrogen chloride oxidation reactor 6 and the hydrochloric gas discharged to the hydrogen chloride absorbing column 5 is properly determined based on an ability of the hydrogen chloride oxidation reactor 6 to produce chlorine and an ability of hydrogen chloride absorbing column 5 to produce hydrochloric acid.

The hydrogen chloride oxidation reactor 6 is not limited to any particular one as long as it is a reactor tank for oxidizing the hydrochloric gas to produce chlorine ($Cl_2$). For example, the hydrogen chloride oxidation reactor 6 includes a fluid bed reactor using chromium oxide as a catalyst and a fixed bed reactor using ruthenium oxide as the catalyst. The hydrogen chloride oxidation reactor 6 is connected to the carbonyl chloride producing reactor 2 via a re-supply line 13 and connected to the hydrogen chloride absorbing tank 5 via a hydrochloric acid connection line 14.

When the hydrogen chloride oxidation reactor 6 is comprising the fluid bed reactor, at least 0.25 mol of oxygen per mol of hydrogen chloride contained in the hydrochloric gas is supplied to the fluid bed reactor, for a reaction in the presence of chromium oxide at 0.1-5 MPa-gauge and 300-500° C. with reference to Japanese Laid-open (Unexamined) Patent Publication No. Sho 62-275001, for example. An amount of hydrochloric gas supplied is in a range of e.g. 0.2-1.8 $Nm^3$/h·kg-catalyst.

When the hydrogen chloride oxidation reactor 6 is comprising the fixed bed reactor, at least 0.25 mol of oxygen per mol of hydrogen chloride contained in the hydrochloric gas is supplied to the fixed bed reactor, for a reaction in the presence of a ruthenium-containing catalyst at 0.1-5 MPa and 200-500° C. with reference to Japanese Laid-open (Unexamined) Patent Publication No. 2000-272906, for example.

Then, in the hydrogen chloride oxidation reactor 6, the hydrochloric gas is oxidized by oxygen ($O_2$), whereby chlorine is produced and water ($H_2O$) is produced secondarily. As a result of this, chlorine and hydrochloric acid (an aqueous solution of hydrogen chloride: $HCl/H_2O$) are produced. In this oxidation reaction, a conversion ratio of hydrochloric gas to chlorine is e.g. 60% or more, or preferably 70-95%.

Then, in the polyisocyanate production system 1, the chlorine obtained in the hydrogen chloride oxidation reactor 6 is supplied to the carbonyl chloride producing reactor 2 via the re-supply line 13 and is reused as a raw material for producing carbonyl chloride in the carbonyl chloride producing reactor 2. When the chlorine thus obtained is reused as the raw material of the carbonyl chloride, the chlorine can be recycled without being discharged to the outside of the system of the polyisocyanate production system 1. This enables an efficient use of the hydrochloric gas produced secondarily, while reducing environmental loads.

In this polyisocyanate production system 1, chlorine (additional chlorine) prepared separately as a raw material is also supplied to the carbonyl chloride producing reactor 2 according to need, other than the chlorine (the recycled chlorine) supplied thereto from the hydrogen chloride oxidation reactor 6 via the re-supply line 13. The additional chlorine may be purchased from outside. Alternatively, a separate chlorine production apparatus using a process such as electrolyzation may be provided so as to supply the additional chlorine therefrom.

Although unoxidized (unreacted) hydrochloric gas and hydrochloric acid produced secondarily in the hydrogen chloride oxidation reactor 6 may be provided to a production of hydrochloric acid of a predetermined concentration in the hydrogen chloride oxidation reactor 6 for industrial use or other process as an acid catalyst of polymethylenepolyphenylene polyamine (MDA), the unoxidized (unreacted) hydrochloric gas and the hydrochloric acid produced secondarily in the hydrogen chloride oxidation reactor 6 are supplied to the hydrogen chloride absorbing column 5 via the hydrochloric acid connection line 14, for example.

That is, the hydrochloric gas is converted to chlorine at a constant conversion ratio in the hydrogen chloride oxidation reactor 6. Accordingly, the unoxidized (unreacted) hydrochloric gas and the hydrochloric acid produced secondarily corresponding to the rest from hydrochloric gas converted to the chlorine are supplied from the hydrogen chloride oxidation reactor 6 to the hydrogen chloride absorbing column 5 via the hydrochloric acid connection line 14 at a fixed ratio. For example, where a conversion ratio in the hydrogen chloride oxidation reactor 6 is 80%, 80% of the hydrochloric gas is converted to chlorine in the hydrogen chloride oxidation reactor 6, while on the other hand, the unoxidized (unreacted) hydrochloric gas and the hydrochloric acid produced secondarily corresponding to the remaining 20% of the hydrochloric gas are supplied therefrom to the hydrogen chloride absorbing column 5 via the hydrochloric acid connection line 14.

The hydrogen chloride absorbing column 5 is not limited to any particular one as long as it can adjust a hydrochloric acid solution (a solution of hydrogen chloride: HClaq) by absorbing hydrochloric gas in water, and comprised of a known absorbing column.

In the hydrogen chloride absorbing column 5, hydrochloric gas discharged from the hydrogen chloride purifying tank 4 via the first hydrochloric-gas connection line 10 and the unoxidized (unreacted) hydrochloric gas supplied from the hydrogen chloride oxidation reactor 6 via the hydrochloric acid connection line 14 are absorbed in water to thereby produce hydrochloric acid. In addition to these, hydrochloric acid produced secondarily supplied from the hydrogen chloride oxidation reactor 6 via the hydrochloric acid connection line 14 is also added thereto. The hydrochloric acid obtained, as it is, or purified by an activated carbon and the like, is provided for industrial use.

When the unoxidized hydrochloric gas in the hydrogen chloride oxidation reactor 6 and the hydrochloric acid produced therein are supplied to the hydrogen chloride absorbing column 5 without being discharged in the manner described above, hydrochloric acid can be produced effectively, while utilizing an efficient use of surplus hydrochloric gas. When the hydrochloric acid is produced from the surplus hydrochloric gas in the hydrogen chloride oxidation reactor 6, the surplus hydrochloric gas can be detoxified while the hydrochloric acid produced therefrom can be reused. As a result of this, an effective use of the surplus hydrochloric gas can be realized.

A water supply line 15 for supplying water for the hydrochloric gas to be absorbed therein, a hydrochloric acid discharge line 16 for discharging the hydrochloric acid obtained, and a hydrochloric acid back-flow line 17 one end of which is connected to the hydrochloric acid discharge line 16 and other end of which is connected to the hydrogen chloride absorbing column 5 are connected to the hydrogen chloride absorbing column 5. A water supply regulating valve 18 is interposed in the water supply line 15, and a back-flow regulating valve 19 is interposed in the hydrochloric acid back-flow line 17. A concentration sensor 20 is interposed in the hydrochloric acid discharge line 16. The water supply regulating valve 18, the back-flow regulating valve 19, and concentration sensor 20 are connected to a concentration control unit 21, which serve as hydrochloric acid concentration adjusting unit.

In the hydrogen chloride absorbing column 5, water is supplied to from the water supply line 15, and the hydrochloric gas discharged from the hydrochloric acid purifying tank 4 via the first hydrochloric gas connection line and the unoxidized (unreacted) hydrochloric gas supplied thereto from the hydrogen chloride oxidation reactor 6 via the hydrochloric acid connection line 14 are absorbed in the water. Thereafter, the hydrochloric acid thus obtained is discharged from the hydrochloric acid discharge line 16. Further, a part of the hydrochloric acid flows back to the hydrogen chloride absorbing column 5 without being discharged from the hydrochloric acid discharge line 16.

In the hydrogen chloride absorbing column 5, a concentration of the hydrochloride acid discharged from the hydrochloric acid discharge line 16 is monitored by the concentration sensor 20. The concentration of the hydrochloride acid is input to the concentration control unit. The concentration control unit 21 controls the water supply regulating valve 18 and the back-flow regulating valve 19 based on the input concentration of the hydrochloric acid to adjust an amount of water supplied from the water supply line 15 and an amount of hydrochloric acid flown back from the hydrochloric acid discharge line 16, whereby the concentration of the hydrochloric acid discharged from the hydrochloric acid discharge line 16 is adjusted to a desired concentration.

When the concentration of the hydrochloric acid discharged from the hydrochloric acid discharge line 16 is adjusted to a desired concentration as is described, the hydrochloric acid of stable quality can be produced. The hydrochloric acid of a concentration thus adjusted to e.g. 30-37 weight % can be used as it is for industrial use.

The detoxification column 7 includes a treatment tank 26, a storage tank 27, and a pump 28. The treatment tank 26 has a gas-liquid contact chamber 29 in which a packed material is packed to improve an efficiency of gas-liquid contact and also has showers 30 arranged over the gas-liquid contact chamber 29. A bottom of the treatment tank 26, the storage tank 27, the pump 28, and the showers 30 are connected via a circulation line 31.

A sodium hydroxide aqueous solution (NaOHaq.) for detoxifying the hydrochloric gas is stored in the storage tank 27. The sodium hydroxide aqueous solution is first pumped up by the pump 28 flowing upward through the circulation line 31, and sprayed from the showers 30 into the gas-liquid contact chamber 29 of the treatment tank 26. After passing through the gas-liquid contact chamber 29, the sodium hydroxide aqueous solution flows back to the storage tank 27 from the bottom of the treatment tank 26. The sodium hydroxide aqueous solution is circulated in the sequence as described. A part of the sodium hydroxide aqueous solution is discharged from the circulation line 31 to adjust a concentration of the sodium hydroxide aqueous solution in the storage tank 27 to a predetermined concentration of e.g. 5-30%.

On the other hand, the third hydrochloric gas connection line 12 is connected to the treatment tank 26 so as to flow upward from the bottom of the gas-liquid contact chamber 29. The detoxification column 7 and the hydrogen chloride absorbing column 5 are connected in parallel to the hydrogen chloride purifying tank 4. When an abnormality is in the hydrogen chloride oxidation reactor 6, the hydrochloric gas discharged from the third hydrochloric gas connection line 12 is supplied to the detoxification column 7 so as to contact with the sodium hydroxide aqueous solution sprayed from the showers 30 in the gas-liquid contact chamber 29 in the vertically opposite direction for an effective gas-liquid contact to detoxify the hydrochloric gas. Thereafter, the resultant gas is discharged from the treatment tank 26 to the atmosphere.

As described above, in this polyisocyanate production system 1, when an abnormality of the hydrogen chloride oxidation reactor 6 is not detected by the pressure sensor 25, the hydrochloric gas purified by the hydrogen chloride purifying tank 4 is supplied to the hydrogen chloride oxidation reactor 6. Then, chlorine is produced from the hydrochloric gas supplied in the hydrogen chloride oxidation reactor 6 and discharged to the hydrogen chloride absorbing column 5. Then, the hydrochloric acid is produced from the hydrochloric gas discharged in the hydrogen chloride absorbing column 5. The hydrochloric gas is detoxified in the processes described above.

On the other hand, when an abnormality is in the hydrogen chloride oxidation reactor 6 and then an amount of the hydrogen chloride exceeds the treating capability of the hydrogen chloride absorbing column 5, so that the abnormality of the hydrogen chloride oxidation reactor 6 is detected by the pressure sensor 25, the hydrochloric gas control unit 32 controls the valve 24 to discharge the hydrogen chloride from the hydrogen chloride purifying tank 4 to the detoxification column 7, so as to adjust the pressure of the hydrogen chloride purifying tank 4 to a predetermined pressure. As a result of this, the hydrochloric gas supplied to the hydrogen chloride oxidation reactor 6 in the interim is discharged to the detoxification column 7 and is detoxified in the detoxification column 7. As a result, when the hydrogen chloride oxidation reactor 6 is in normal, the hydrochloric gas can be supplied steadily to the hydrogen chloride oxidation reactor 6, while a surplus of the hydrochloric gas is detoxified in the hydrogen chloride absorbing column 5. When a trouble occurs in the hydrogen chloride oxidation reactor 6, the hydrochloric gas supplied to the hydrogen chloride oxidation reactor 6 in the interim is detoxified in the detoxification column 7. Thus, a large amount of hydrochloric gas supplied to the hydrogen chloride oxidation reactor 6 in the interim can be detoxified according to the ability of the hydrogen chloride absorbing column 5 to produce the hydrochloric acid, thus achieving an effective treatment of the hydrochloric gas.

When an abnormality of the hydrogen chloride oxidation reactor 6, such as a temperature anomaly of the hydrogen chloride oxidation reactor 6, is detected, the hydrogen chloride oxidation reactor 6 is operated for an interlock control to stop the production of chlorine. Also, the detoxification column 7 is set to detoxify the hydrochloric gas for a predetermined time (e.g. 30 minutes), during which the production of polyisocyanate in the isocyanate producing reactor 3 is shut down stably to secure a safe shutdown.

In this polyisocyanate production system 1, when the hydrogen chloride oxidation reactor 6 is in normal, the hydrochloric gas control unit 32 controls the flow-rate control valve 23 to keep (e.g. 90 where the hydrochloric gas purified in the hydrogen chloride purifying tank 4 is taken to be 100) an amount of hydrochloric gas supplied from the hydrogen chloride purifying tank 4 to the hydrogen chloride oxidation reactor 6 via the second hydrochloric-gas connection line 11 to be constant. At the same time, the hydrochloric gas control unit 32 also controls the pressure control valve 22 based on the inner pressure of the hydrogen chloride purifying tank 4 input from the pressure sensor 25 to discharge the hydrochloric gas from the hydrogen chloride purifying tank 4 to the hydrogen chloride absorbing column 5 via the first hydrochloric-gas connection line 10 so as to keep the inner pressure of the hydrogen chloride purifying tank 4 (where the hydrochloric gas purified in the hydrogen chloride purifying tank 4 is taken to be 100, the remaining amount (10) of 90 supplied to the second hydrochloric gas connection line 11 is discharged, for example).

When the hydrochloric gas control unit 32 controls the flow-rate control valve 23 and the pressure control valve 22 in the manner described above, the hydrochloric gas is steadily supplied to the hydrogen chloride oxidation reactor 6 at a constant flow-rate, while the surplus of the hydrochloric gas is discharged to the hydrogen chloride absorbing column 5, whereby the inner pressure of the hydrogen chloride purifying tank 4 and thus the inner pressure of the isocyanate producing reactor 3 can be kept constant. As a result, this can produce the chlorine steadily from the hydrochloric gas produced secondarily, while the inner pressure of the isocyanate producing reactor 3 can be kept constant. This enables a stable reaction between carbonyl chloride and polyamine and an effective treatment of the hydrochloric gas produced secondarily.

In this polyisocyanate production system 1, the concentration control unit 21 and the hydrochloric gas control unit 32 are connected via a bus and controlled in a central control unit. This builds a distributed control system of the polyisocyanate production system 1.

Figure 2:
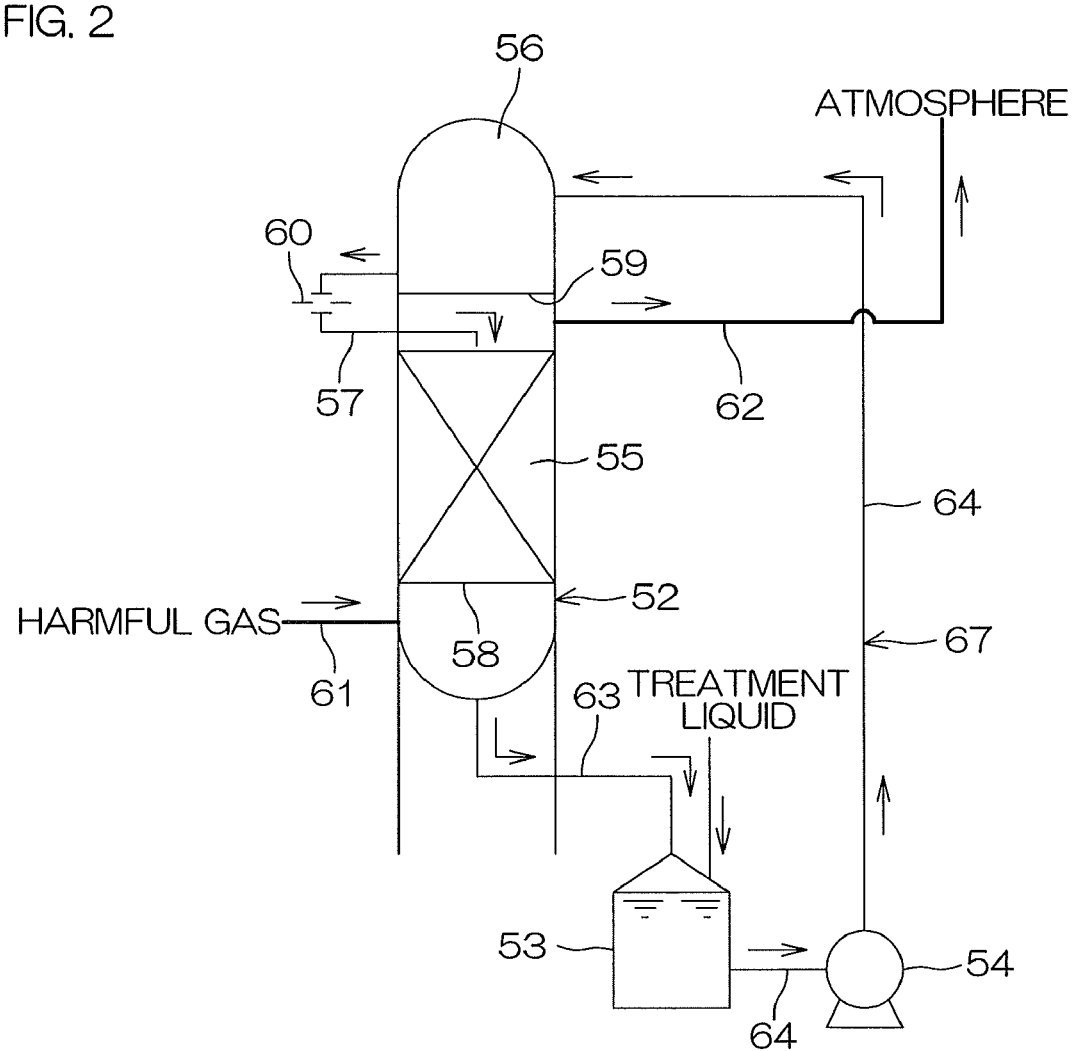
FIG. 2 is a schematic block diagram showing a detoxification column as a first embodiment of the gas treatment apparatus of the present invention.

FIG. 2 is a schematic block diagram showing a detoxification column 51A to detoxify exhaust gases as a first embodiment of the gas treatment apparatus of the present invention.

As shown in FIG. 2, the detoxification column 51A is provided in the plant for producing chemical products in order to detoxify a harmful gas as an exhaust gas produced in the chemical process and then discharge the detoxified gas to atmosphere. The harmful gas includes, for example, a carbonyl-chloride-containing gas and a hydrogen-chloride-containing gas produced in the polyisocyanate production process in the polyisocyanate production plant. Accordingly, the detoxification column 51A can be used as the detoxification column 7 of the polyisocyanate production system 1.

The detoxification column 51A is comprising a treatment tank 52, a storage tank 53, and a solution sending pump 54 used as a power source.

The treatment tank 52 is in a closed cylindrical form extending vertically and closed at its upper end and lower end, comprising a gas-liquid contact chamber 55, a storage chamber 56, and a treatment liquid supply pipe 57 serving as a treatment liquid supply unit.

The treatment tank 52 is provided, at a lower portion thereof, with a packed material support plate 58 for vertically demarking an interior space of the treatment tank 52, and at an upper portion thereof, with a storage chamber bottom plate 59, spaced above from the packed material support plate 58 for vertically demarking the interior space of the treatment tank 52 into the gas-liquid contact chamber 55 and the storage chamber 56. The packed material support plate 58 has a number of air (liquid) vents bored therein.

The gas-liquid contact chamber 55 is defined as an interior space of the treatment tank 52 between the packed material support plate 58 and the storage chamber bottom plate 59. In the gas-liquid contact chamber 55, packed materials such as a Raschig ring, a Berl saddle and the like, are packed on the packed material support plate 58 to a level to leave a space between the packed material and the storage chamber bottom plate 59.

The storage chamber 56 is defined as an interior space of the treatment tank 52 located above the storage chamber bottom plate 59.

The treatment liquid supply pipe 57, one end of which is connected to a lower portion of the storage chamber 56 and the other end of which is inserted in the gas-liquid contact chamber 55, is located above the packed material. A restriction orifice 60 for restricting a flow-rate of the treatment liquid flowing through the treatment liquid supply pipe 57 is interposed in the treatment liquid supply pipe 57. At a lower portion of the treatment liquid pipe, a shower or a liquid disperser, though not shown, is provided to spray the treatment liquid uniformly over the packed material.

A harmful gas charge pipe 61 for flowing in the harmful gas to the treatment tank 52 is connected to the treatment tank 52 at a lower side of the packed material support plate 58, or on the underside of the gas-liquid contact chamber 55. A treatment gas discharge pipe 62 for flowing out the harmful gas detoxified (hereinafter it is referred as the treated gas) to from the treatment tank 52 is connected to the treatment tank 52 at a lower side of the storage chamber bottom plate 59, or above of the packed material in the gas-liquid contact chamber 55.

The treatment liquid for detoxifying the harmful gas is stored in the storage tank 53. When the harmful gas is, for example, the carbonyl-chloride-containing gas or the hydrogen-chloride-containing gas cited above, an alkaline aqueous solution, such as a sodium hydroxide aqueous solution or a potassium hydroxide aqueous solution, is used as the treatment liquid. The treatment liquid is properly re-supplied to the storage tank 53 according to a circulating amount of the treatment liquid.

A back-flow pipe 63, one end of which is connected to a lower end of the treatment tank 52, is connected to the storage tank 53 at the other end thereof. The storage tank 53 is connected to the treatment tank 52 via the back-flow pipe 63. A transport pipe 64, one end of which is connected to the storage chamber 56 located above the treatment tank 52, is connected to the storage tank 53 at the other end thereof. The storage tank 53 is connected to the storage chamber 56 via the transport pipe 64.

The solution sending pump 54 is not limited to any particular one as long as it can send a liquid, including a reciprocating pump, a centrifugal pump, and a rotary pump. The solution sending pump 54 is interposed in the transport pipe 64.

Now, reference is given to a continuous steady operation of the detoxification column 51A.

In the detoxification column 51A, when the solution sending pump 54 is driven, the treatment liquid is pumped up from the storage tank 53 and sent to the storage chamber 56 through the transport pipe 64.

The treatment liquid sent to the interior of the storage chamber 56 flows in the treatment liquid supply pipe 57. After a flow-rate of the treatment liquid is restricted by the restriction orifice 60, the treatment liquid discharged from the treatment liquid supply pipe 57 with a gravity-drop and is sprayed over the packed material from above in the interior of the gas-liquid contact chamber 55. At this time, an overflow line may be provided in the storage chamber 56 so that an overflowing treatment liquid can also be sprayed in the gas-liquid contact chamber 55.

On the other hand, the harmful gas flows into the treatment tank 52 from the harmful gas charge pipe 61 and then flows into the gas-liquid contact chamber 55 via the air vents of the packed material support plate 58 passing through spaces between the packed materials from bottom to top. As a result of this, the harmful gas contacts with the treatment liquid sprayed from above in the vertically opposite direction for an effective gas-liquid contact to detoxify the harmful gas. For example, in the case that the harmful gas is the carbonyl-chloride-containing gas and the treatment liquid is a sodium hydroxide aqueous solution, when these undergo the gas-liquid contact, sodium chloride and sodium carbonate are produced and the harmful gas is detoxified. Thereafter, the treated gas is discharged to the atmosphere via the treated gas discharge pipe 62.

Thereafter, the treatment liquid dropping from the interior of the gas-liquid contact chamber 55 via the air vents of the packed material support plate 58 returns to the storage tank 53 from the lower end of the treatment tank 52 via the back-flow pipe 63. As seen from above, in the detoxification column 51A, a circulation line 67 serving as a treatment liquid back-flow unit is composed by the transport pipe 64 and the back-flow pipe 63. The treatment liquid is circulated through the circulation line 67 by the drive of the solution sending pump 54.

When the treatment liquid is circulated in the manner described above, waste of the treatment liquid can be minimized to reduce running costs.

In this detoxification column 51A, the continuous steady operation is continued usually. In this detoxification column 51A, even when the drive of the solution sending pump 54 is stopped due to a trouble, such as an electric power failure and a malfunction so as that the circulation of the treatment liquid through the circulation line 67 is stopped, since the storage chamber 56 is located over the gas-liquid contact chamber 55, the treatment liquid stored in the storage chamber 56 drops by gravity into the gas-liquid contact chamber 55 through the treatment liquid supply pipe 57 without requiring any specific power source. Then, the treatment liquid is supplied to the interior of the gas-liquid contact chamber 55 via the treatment liquid supply pipe 57 until the treatment liquid in the storage chamber 56 runs out. Thus, even when the supply of the treatment liquid to the gas-liquid contact chamber 55 is interrupted due to a trouble resulted from the solution sending pump 54, the gas-liquid contact between the treatment liquid and the harmful gas in the gas-liquid contact chamber 55 can be continued to continue the treatment of the harmful gas, thus providing a further improvement in safety.

Even when the treatment liquid in the storage chamber 56 runs out, since residual treatment liquid remains in the gas-liquid contact chamber 55, the harmful gas can be detoxified until such residual treatment liquid is consumed.

When a power failure or a malfunction occurs during the time the harmful gas is detoxified by the treatment liquid stored in the storage chamber 56, the treatment liquid may be circulated again by switching the power to an auxiliary power in the power failure or by driving to another liquid sending pump in the malfunction.

The flow-rate of the harmful gas flowing into the treatment tank 52 from the harmful gas charge pipe 61 and the flow-rate of the treatment liquid circulated by the solution sending pump 54 are properly determined depending on the types of the harmful gas or the treatment liquid, and the types of the treatment for detoxification.

Also, an amount of treatment liquid stored in the storage chamber 56 is properly determined depending on the types of the harmful gas or the treatment liquid, and the treatment quantity of the plant.

Figure 3:
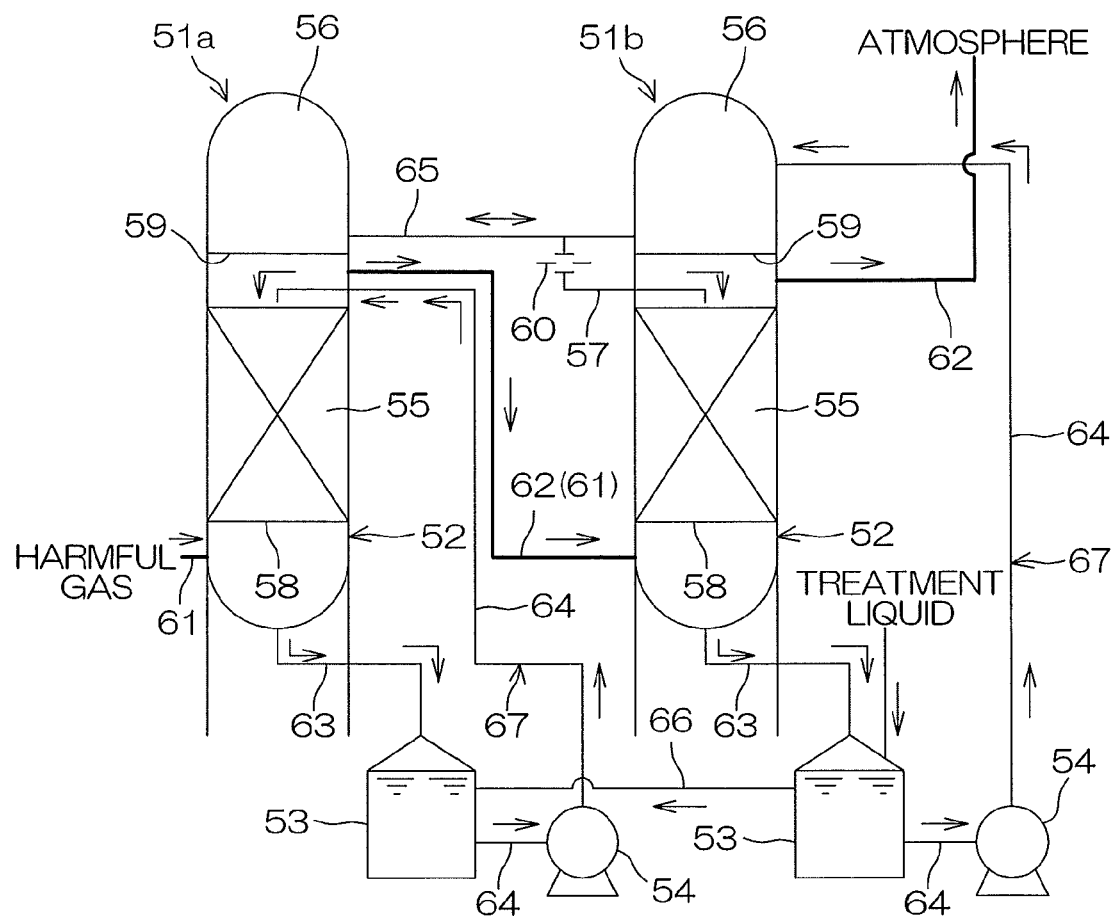
FIG. 3 is a schematic block diagram showing a detoxification column as a second embodiment of the gas treatment apparatus of the present invention.

FIG. 3 is a schematic block diagram showing a detoxification column 51B as a second embodiment of the gas treatment apparatus of the present invention. In FIG. 3, the same numerals refer to corresponding members to those shown in FIG. 2 and the description thereon is omitted.

The detoxification column 51B is configured as a double-stage continuous detoxification column, comprising a first-stage detoxification column 51a and a second-stage detoxification column 51b which are connected in series in a flowing direction of the harmful gas.

The first-stage detoxification column 51a is comprising a treatment tank 52, a storage tank 53, and a solution sending pump 54, as is the case with the detoxification column 51 of the first embodiment.

However, the treatment tank 52 of the first-stage detoxification column 51a is not provided with a treatment liquid supply pipe 57. Instead, an end of a transport pipe 64 is inserted in a gas-liquid contact chamber 55 and is located above a packed material (the first-stage detoxification column 51a may be provided with the treatment liquid supply pipe 57, if needed). A shower or a liquid disperser, though not shown, is provided at the end of the transport pipe 64 to spray the treatment liquid uniformly over the packed material.

The second-stage detoxification column 51B is also provided with a treatment tank 52, a storage tank 53, and a solution sending pump 54, as is the case with the first embodiment. The second-stage detoxification column 51b has the same configuration as that of the detoxification column 51 of the first embodiment.

In the detoxification column 51B, a treated gas discharge pipe 62 of the first-stage detoxification column 51a serves a harmful gas charge pipe 61 of the second-stage detoxification column 51b as a gas passage path is connected to the second-stage harm removing tank 51b at a lower side the gas-liquid contact chamber 55 of the treatment tank 52 of the second-stage detoxification column 51b.

In this detoxification column 51B, a storage chamber 56 of the first-stage detoxification column 51a and a storage chamber 56 of the second-stage detoxification column 51b are connected with each other via a storage chamber communication pipe 65. The storage chamber communication pipe 65 is connected at one end thereof to the storage chamber 56 of the first-stage detoxification column 51a and is connected at the other end to the treatment liquid supply pipe 57 of the second-stage detoxification column 51 at a mid-location thereof (upstream of the restrict orifice 60). The storage chamber 56 of the first-stage detoxification column 51a and the storage chamber 56 of the second-stage detoxification column 51b communicate with each other via the storage chamber communication pipe 65. The storage chamber communication pipe 65 is used for detoxification in the second-stage detoxification column 51b.

Also, in the detoxification column 51B, the storage tank 53 of the first-stage detoxification column 51a and the storage tank 53 of the second-stage detoxification column 51b are connected with each other via a storage tank communication pipe 66. The storage tank communication pipe 66 is connected at one end thereof to the storage tank 53 of the first-stage detoxification column 51a and is connected at the other end to the storage tank 53 of the second-stage detoxification column 51b. The storage tank 53 of the first-stage detoxification column 51a and the storage tank 53 of the second-stage detoxification column 51b communicate with each other via the storage tank communication pipe 66. As a result of this, the treatment liquids of the both storage tanks 53 are increased or decreased equally so that liquid levels (water levels) of the both storage tanks 53 correspond to each other.

Now, reference is given to a continuous steady operation of the detoxification column 51B.

In the first-stage detoxification column 51a of this detoxification column 51B, when the solution sending pump 54 is driven, the treatment liquid is pumped up from the storage tank 53 and is sprayed over the packed material from above of the packed material in the gas-liquid contact chamber 55 via the transport pipe 64.

The treatment liquid thus sprayed contacts with the harmful gas which flows in from the harmful gas charge pipe 61 and passes through the spaces between the packed materials packed in the gas-liquid contact chamber 55 from bottom toward top in the vertically opposite direction for an effective gas-liquid contact, thereby detoxifying the harmful gas. In the detoxification column 51B, a detoxification rate of the harmful gas in the first-stage detoxification column 51b is set to be less than 100%, then the harmful gas is detoxified completely by detoxifying the remaining harmful gas in the next second-stage detoxification column 51b.

Thereafter, the harmful gas detoxified in the first-stage detoxification column 51a, or the treated gas is flown into the treatment tank 52 of the second-stage detoxification column 51b through the treated gas discharge pipe 62 of the first-stage detoxification column 51a (the harmful gas charge pipe 61 of the second-stage detoxification column 51b).

The treatment liquid is returned to the storage tank 53 from the lower end of the treatment tank 52 through the back-flow pipe 63 and is circulated through the circulation line 67 formed by the transport pipe 64 and the back-flow pipe 63.

In the second-stage detoxification column 51b, when the solution sending pump 54 is driven, the treatment liquid is pumped up from the storage tank 53 and transported to the storage chamber 56 through the transport pipe 64.

The treatment liquid sent to the interior of the storage chamber 56 flows in the treatment liquid supply pipe 57. After a flow-rate of the treatment liquid is restricted by the restriction orifice 60, the treatment liquid is discharged from the treatment liquid supply pipe 57 with a gravity-drop and is sprayed over the packed material from above of the packed material in the gas-liquid contact chamber 55. At this time, an overflow line may be provided in the storage chamber 56 so that an overflowing treatment liquid can also be sprayed in the gas-liquid contact chamber 55.

The treatment liquid thus sprayed contacts with the harmful gas which flows in from the treated gas discharge pipe 62 of the first-stage detoxification column 51a (the harmful gas charge pipe 61 of the second-stage detoxification column 51b) and passes through the spaces between the packed materials packed in the gas-liquid contact chamber 55 from bottom toward top in the vertically opposite direction for an effective gas-liquid contact, thereby detoxifying the harmful gas completely.

Thereafter, the harmful gas detoxified in the second-stage detoxification column 51b, or the treated gas is discharged to atmosphere via the treated gas discharge pipe 62.

The treatment liquid is returned to the storage tank 53 from the lower end of the treatment tank 52 through the back-flow pipe 63 and is circulated through the circulation line 67 formed by the transport pipe 64 and the back-flow pipe 63.

In the detoxification column 51B as well, even when the drive of the both solution sending pumps 54 are stopped due to a trouble, such as an electric power failure and a malfunction so as that the treatment liquid is not circulated through the circulation lines 67, the treatment liquid stored in the storage chamber 56 drops by gravity into the gas-liquid contact chamber 55 in the second-stage detoxification column 51b immediately before the treated gas is discharged to atmosphere (i.e., one in the detoxification column of the multistage continuous detoxification column located at a most downstream side with respect to a flowing direction of the harmful gas) through the treatment liquid supply pipe 57 without requiring any specific power source, so that the gas-liquid contact between the treatment liquid and the harmful gas is continued. Thus, as is the case with the detoxification column 51A of the first embodiment, even when the supply of the treatment liquid to the gas-liquid contact chamber 55 is interrupted due to a trouble resulted from the solution sending pump 54, the gas-liquid contact between the treatment liquid and the harmful gas in the gas-liquid contact chamber 55 can be continued to continue the treatment of the harmful gas, thus providing a further improvement in safety.

Also, in the detoxification column 51B, a detoxification rate of the harmful gas in the first-stage detoxification column 51*b* is set to be less than 100%, then the harmful gas is detoxified completely by detoxifying the remaining harmful gas in the next second-stage detoxification column 51*b*. Hence, the treatment of detoxifying the harmful can be carried out multistage-wise and continuously, thus achieving an effective treatment of the harmful gas.

In the detoxification column 51B of the second embodiment in which only the second-stage detoxification column 51*b* is provided with the treatment liquid supply pipe 57 for a gravity drop of the treatment liquid, the first-stage detoxification column 51*a* may also be provided with a corresponding treatment liquid supply pipe 57 for a gravity drop of the treatment liquid. However, the illustrated embodiment wherein only the second-stage detoxification column 51*b* immediately before the treated gas is discharged to atmosphere (i.e., one in the detoxification column of the multistage continuous detoxification column located at a most downstream side with respect to a flowing direction of the harmful gas) is provided with the treatment liquid supply pipe 57 for a gravity drop of the treatment liquid can provide an advantage of providing a simplified structure of the system, while proving a further improved safety in the treatment of the harmful gas.

INDUSTRIAL APPLICABILITY

The polyisocyanate production system of the present invention is suitably used as a production apparatus for producing polyisocyanate used as a raw material of polyurethane.

Also, the gas treatment apparatus of the present invention is suitably used as the apparatus for treating gas such as, for example, detoxifying a harmful gas produced in a chemical process in the chemical product producing plant.

The invention claimed is:

1. A gas treatment apparatus for treating a gas by bringing the gas into contact with a treatment liquid, the gas treatment apparatus comprising:
   a plurality of treatment tanks,
   the plurality of treatment tanks each comprising:
   a gas-liquid contact chamber for a gas-liquid contact of the gas with the treatment liquid,
   a storage chamber, located over the gas-liquid contact chamber, for storing the treatment liquid, and
   a storage chamber bottom plate dividing the interior space of the treatment tank for defining the gas-liquid contact chamber and the storage chamber is provided in the treatment tank,
   wherein the gas-liquid contact chamber is defined as an interior space of the treatment tank located below the storage chamber bottom plate,
   the storage chamber is defined as an interior space of the treatment tank located above the storage chamber bottom plate,
   a gas passage path for passing the gas in series through the respective gas-liquid contact chambers is further provided,
   at least one treatment tank located at a most downstream side with respect to a flowing direction of the gas flowing along the gas passage path is provided with a treatment liquid supply pipe that supplies the treatment liquid to the gas-liquid contact chamber from the storage chamber,
   the plurality of storage chambers are connected with each other via a storage chamber communication pipe, and
   one end of the storage chamber communication pipe at a most downstream side is connected to the storage chamber located upstream of the storage chamber at a most downstream side, and the other end of the storage chamber communication pipe at a most downstream side is connected to the treatment liquid supply pipe.

2. The gas treatment apparatus according to claim 1, which further comprises a treatment liquid back-flow unit for returning the treatment liquid discharged from the gas-liquid contact chamber to the storage chamber.

3. The gas treatment apparatus according to claim 1, wherein the gas is carbonyl-chloride-containing gas, and the treatment liquid is an alkaline.

4. The gas treatment apparatus according to claim 1,
   wherein one end of the treatment liquid supply pipe is connected to a side wall at a lower portion of the storage chamber, and the other end of the treatment liquid supply pipe is inserted in the gas-liquid contact chamber from a side wall thereof, whereby the treatment liquid supply pipe supplies the treatment liquid in the storage chamber to an inside of the gas-liquid contact chamber with a gravity-drop,
   a restriction orifice is interposed in the treatment liquid supply pipe for restricting a flow-rate of the treatment liquid flowing in the treatment liquid supply pipe, and
   the other end of the storage chamber communication pipe at a most downstream side is connected upstream of the restriction orifice in the treatment liquid supply pipe.

* * * * *